US012590916B2

(12) United States Patent
Marti Sauras et al.

(10) Patent No.: US 12,590,916 B2
(45) Date of Patent: Mar. 31, 2026

(54) ELECTRIC POTENTIAL MEASUREMENT SYSTEM FOR CONTINUOUSLY MEASURING THE ELECTRIC POTENTIAL OF THE GROUND

(71) Applicant: GLOBAL CEN TECHNOLOGIES SL, Santa María del Camí (ES)

(72) Inventors: José María Marti Sauras, Binissalem (ES); David Bosch Ros, Sabadell (ES); Álvaro Sanz Gómez, Palma (ES)

(73) Assignee: GLOBAL CEN TECHNOLOGIES SL, Santa María del Camí (ES)

( * ) Notice: Subject to any disclaimer, the term of this patent is extended or adjusted under 35 U.S.C. 154(b) by 269 days.

(21) Appl. No.: 18/291,179

(22) PCT Filed: Jul. 23, 2021

(86) PCT No.: PCT/ES2021/070557
§ 371 (c)(1),
(2) Date: Jan. 22, 2024

(87) PCT Pub. No.: WO2023/002071
PCT Pub. Date: Jan. 26, 2023

(65) Prior Publication Data
US 2024/0393277 A1      Nov. 28, 2024

(51) Int. Cl.
G01N 27/04        (2006.01)
G01N 27/60        (2006.01)
            (Continued)

(52) U.S. Cl.
CPC ........... G01N 27/041 (2013.01); G01N 27/04 (2013.01); G01N 27/60 (2013.01); G01N 33/24 (2013.01); G01S 19/49 (2013.01); G01V 3/088 (2013.01)

(58) Field of Classification Search
CPC ...... G01N 27/041; G01N 33/24; G01N 27/04; G01N 27/60; G01S 19/49; G01V 3/088
See application file for complete search history.

(56)                References Cited

U.S. PATENT DOCUMENTS 4,415,857 A * 11/1983 Cordell ..................... G01V 3/24
                                              324/357
4,945,310 A *  7/1990 Jackson ................... G01V 3/15
                                              324/349

(Continued)

FOREIGN PATENT DOCUMENTS

CN        110989008 A      4/2020
CN        212781256 U      3/2021

OTHER PUBLICATIONS

International Search Report and Written Opinion for Corresponding International Patent Application No. PCT/ES2021/070557, 11 pages, mailed Apr. 12, 2022.

*Primary Examiner* — Amy He
(74) *Attorney, Agent, or Firm* — LUCAS & MERCANTI, LLP

(57)                ABSTRACT

An electric potential measurement system for detecting contaminants in the subsoil, comprising: a reference electrode (2); a vehicle (3); a measurement electrode (4), with: a contact electrode (7) formed by an electrically insulating container (13) including a metal electrode (14) surrounded by a non-metal filler material (15), and a retaining mesh (16) covering the base of the container (13); a non-metal contact appendage (9) establishing continuous galvanic contact with the soil as the vehicle (3) moves over the ground (6); a data acquisition and positioning system (5) which acquires and stores position data ($P_i$) and electric potential difference measurements ($\Delta v_i$) between the reference electrode (2) and the measurement electrode (4) in a memory (29). The data stored in the memory can be used to obtain an electric (Continued)

potential map (30) and/or a map (32) with the probability of the presence of contaminants.

14 Claims, 9 Drawing Sheets

(51) Int. Cl.
 *G01N 33/24* (2006.01)
 *G01S 19/49* (2010.01)
 *G01V 3/08* (2006.01)

(56) References Cited

U.S. PATENT DOCUMENTS

| | | | |
|---|---|---|---|
| 2010/0225341 A1 | 9/2010 | Burrows et al. | |
| 2016/0363549 A1 | 12/2016 | Mazzeo et al. | |

* cited by examiner

Electric potential
(mV)

| 1 | 18 | 180 | 184 | 186 | 180 | 181 | 187 | 183 | 181 | 183 | 187 | 181 | 183 |
|---|----|-----|-----|-----|-----|-----|-----|-----|-----|-----|-----|-----|-----|
| 2 | 50230 | 190 | 187 | 185 | 190 | 189 | 185 | 189 | 188 | 186 | 186 | 190 | 187 |
| 3 | 509363 | 187 | 183 | 187 | 188 | 185 | 184 | 189 | 185 | 183 | 188 | 188 | 183 |

Fig. 8A

| 998 | 1 | $GNRMC,090809.00,A,4237.28791,N,00112.75331,W,0.011,220920,,,R,V*10 |
|-----|---|---------------------------------------------------------------------|
| 2003 | 2 | $GNRMC,090810.00,A,4237.28791,N,00112.75331,W,0.018,220920,,,R,V*11 |
| 3001 | 3 | $GNRMC,090811.00,A,4237.28791,N,00112.75331,W,0.017,220920,,,R,V*1F |

Fig. 8B

ELECTRIC POTENTIAL MEASUREMENT SYSTEM FOR CONTINUOUSLY MEASURING THE ELECTRIC POTENTIAL OF THE GROUND

CROSS-REFERENCE TO RELATED APPLICATIONS

This application is a 371 of PCT/ES2021/070557, filed Jul. 23, 2021, the contents of which are incorporated herein by reference.

FIELD OF THE INVENTION

The present invention falls within the field of measurement systems for measuring the physical properties of the subsoil, and particularly electric potential measurement systems for detecting contaminants in the subsoil.

BACKGROUND OF THE INVENTION

The electric potential of points of a ground (or, to be more precise, the electric potential difference between two different points of the ground) depends on several physical properties of the subsoil such as, for example, the electrical resistivity of the materials. The presence of oil pollution affects electric potential, which allows detecting and localising oils.

Rather than providing a continuous measurement of the electric potential of the ground as the measurement equipment moves over the ground to be surveyed, most of the current electric potential measurement systems provide a periodic measurement, with there being a need to stop in order for the measurement equipment to perform the measurement, thus generating a slow, difficult, and laborious measurement process. Furthermore, and unless non-polarisable electrodes are used in these periodic measurement systems for measuring the electric potential, an unwanted polarisation effect in the contact between the ground and the measurement equipment occurs when performing measurement, obtaining an unstable signal which affects the precision of the electric potential measurements.

Other measurement systems based on a wheel with a wound metal wire for continuously measuring the electric potential of the ground as the wheel turns and moves over the ground are also known. However, these continuous measurement systems do not use non-polarisable electrodes, so the polarisation effect between the ground and the measurement equipment negatively affects the precision of the electric potential measurements in a significant manner.

The present invention presents an electric potential measurement system which solves the preceding problems, provides quick, simple, and precise electric potential measurements of the ground as it allows continuously measuring in a simultaneous manner the electric potential as the measurement equipment moves over the ground, and drastically minimising or reducing the polarisation effect in the contact between the ground and the measurement electrode, obtaining a stable and precise signal, representative of the electric potential at each measurement point of the surveyed ground.

DESCRIPTION OF THE INVENTION

The present invention relates to an electric potential measurement system, a geophysical instrument which allows measuring the electric potential on pavements or on unpaved ground, such as asphalt or concrete, which are common in service stations, for the purpose of detecting the presence of contaminants in the subsoil, such as oils.

The use of the present invention requires the prior installation of a reference electrode underground, buried at a specific depth in the ground to be surveyed. The operation of the system consists of moving measurement equipment installed in a vehicle over the ground previously wetted with water. Electric potential survey is a method that is non-invasive (neither the services nor the pavement is damaged), passive and safe (no electric current is injected into the subsoil), quick (the electric potential map is obtained in a short time), and exhaustive (it offers information about the entire surface of a site).

The measurement equipment installed in the vehicle comprises a measurement electrode and a data acquisition and positioning system.

The measurement electrode comprises a contact electrode and a contact appendage. The contact electrode is formed by a container made of an electrically insulating material (e.g., plastic) including therein a metal electrode (e.g., stainless steel) surrounded by a non-metal filler material (e.g., bentonite) with an electrical conductivity less than the electrical conductivity of the metal electrode, and a non-metal retaining mesh covering the base of the container. The retaining mesh is in charge of retaining the filler material and allowing a non-metal electrical contact between the filler material and whatever the retaining mesh is in contact with outside the container (in this case, with an electrically conductive cable connecting the retaining mesh with the contact appendage). The retaining mesh can be, for example, a layer of fabric or a layer of ceramic material. The contact appendage is made of a non-metal material (e.g., a textile material) and is suitable for establishing a continuous galvanic contact with the soil as the vehicle moves over the ground to be surveyed. An electrically conductive cable connects the retaining mesh with the contact appendage. This current conduction pathway within the measurement electrode, from the contact appendage to the metal electrode, prevents the polarisation of the assembly, allowing an electric potential to be quickly measured in the ground without the negative polarisation effect, minimising the polarisation/oxidation of the elements constituting the measurement electrode.

The data acquisition and positioning system comprises a satellite geolocation module and a data processing unit. The satellite geolocation module (e.g., a GPS module) is configured for acquiring a plurality of position data of the vehicle as it moves over the ground. The data processing unit is configured for obtaining a plurality of electric potential difference measurements, representative of the electric potential, between the reference electrode and the measurement electrode as the vehicle moves over the ground. The data acquisition and positioning system is configured for storing in at least one memory the electric potential difference measurements and the position data of the vehicle that are acquired. This data which is stored in the memory can already be used to obtain an electric potential map.

In one embodiment, the data processing unit obtains, from the data acquired and stored in the memory, an electric potential map of the ground by means of associating the electric potential difference measurements with the position data of the vehicle that are acquired. In another embodiment, the data acquisition and positioning system is configured for transmitting, through a communication unit, the data which is stored in the memory to an external device, which is in charge of obtaining the electric potential map.

The processing of the electric potential data acquired by means of the system therefore results in an electric potential map from which a map with the probability of the presence of contaminants (for example, oils) in the subsoil of the surveyed ground can be obtained. This two-dimensional map can be represented by means of colour variation, where the electric potential value increases, for example, from blue to red, as the probability of the presence of oils increases. The contour curves (isolines) of the map indicate the levels of equal electric potential value.

The measurement system of the present invention substantially reduces polarisation as it forces the current to go through a complex electrode, i.e., the measurement electrode, with the particular configuration and structure that has been described. The measurement electrode does not actually prevent polarisation completely, but it does however minimise, slow down, or delay its unwanted effects, given that polarisation would likewise occur but on a much longer time scale, because the metal electrode embedded in the filler material (for example, in bentonite) is already polarised and in electrochemically stable conditions. The only polarisation mechanism that would occur is by ion diffusion through the medium, and this is a very slow process. Moisture difference can also affect polarisation, but by first watering the ground to wet it, this problem is minimised. The temperature is also homogenised and since the measurement is quick, there is no time for thermal equilibrium.

BRIEF DESCRIPTION OF THE DRAWINGS

What follows is a very brief description of a series of drawings that aid in better understanding the invention and which are expressly related to an embodiment of said invention that is shown by way of a non-limiting example of the same.

FIGS. 8A and 8B show the examples of position and electric potential data that are acquired while surveying the ground.

DETAILED DESCRIPTION OF THE INVENTION

Figure 1:
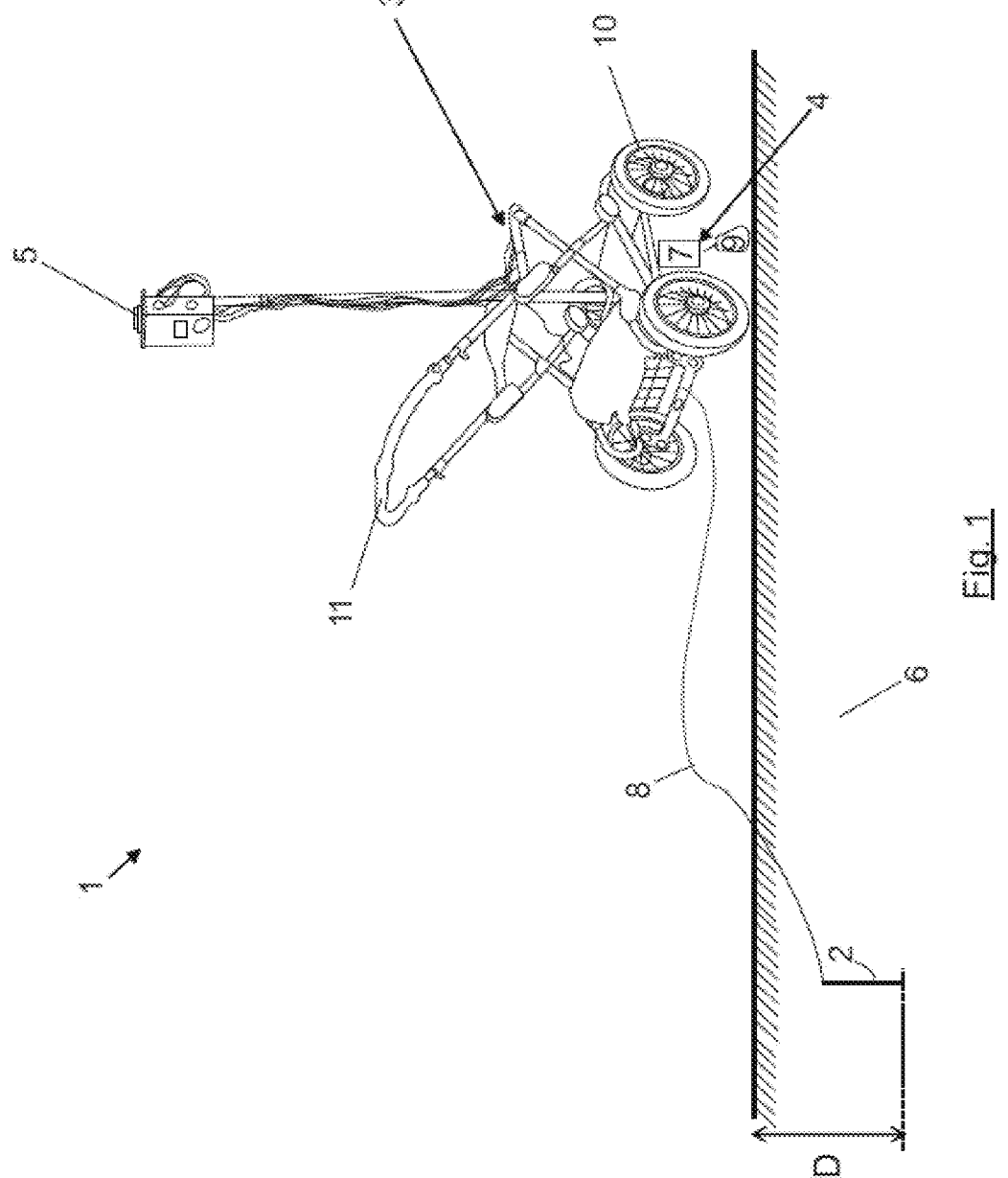
FIG. 1 shows an electric potential measurement system according to an embodiment of the present invention.

FIG. 1 depicts the elements that are part of an electric potential measurement system 1 used for detecting contaminants in the subsoil, according to an embodiment.

The electric potential measurement system 1 comprises a reference electrode 2, a vehicle 3, a measurement electrode 4 (which is a complex electrode or a multiphase electrode formed by different interconnected elements) integral with the vehicle and a data acquisition and positioning system 5 also integral with the vehicle.

The reference electrode 2 is buried in a ground 6 to be surveyed, in which electric potential measurement will be performed, in order to prevent surface thermal variations from causing potential changes in said electrode. In the embodiment shown in FIG. 1, the reference electrode 2 is a metal cylinder, preferably made of stainless steel, to prevent the electrochemical alteration thereof, where one of its ends may have a pointed finish to facilitate insertion into the ground 6. For example, the reference electrode 2 can be a steel cylinder measuring 12 mm in diameter and 25 cm in length, buried in the ground 6 to be surveyed (e.g., under the pavement or in the unpaved ground). For installation, a borehole must first be made with a drill, preferably with a depth D comprised between 50 cm and 100 cm. Alternatively, the reference electrode 2 can be a non-polarisable electrode or the contact electrode 7 which includes the measurement electrode 4.

The reference electrode 2 is connected to the data acquisition and positioning system 5 of the vehicle 3 through a first electrically conductive cable 8 (made of a metal material, for example copper). The reference electrode 2 is used as a common reference or reference potential during the acquisition of electric potential measurement data as the vehicle 3 moves over the ground 6, with the electric potential difference between the reference electrode 2 and each point of the surface of the ground 6 surveyed by a contact appendage 9 of the measurement electrode 4 being measured.

The vehicle 3 may incorporate a cable winding system such as, for example, a bobbin, on which the first cable 8 is wound, such that as the vehicle 3 moves over the ground 6, away from the reference electrode 2, the first cable 8 is gradually unwound from the bobbin to allow the free movement of the vehicle 3. Alternatively, the cable can be kept unwound, although in a more or less organised manner so as to not hinder the movement cars or the transit of people.

The vehicle 3 depicted in FIG. 1 has a four-wheel drive system 10 with hard rubber wheels and a grip handle 11 to manually push or pull the vehicle 3. The vehicle has a base for the placement of the contact electrode 7 of the measurement electrode 4, and a support for the data acquisition and positioning system 5, where a support for a GPS antenna can furthermore be included. The function of the vehicle 3 is to support the measurement electrode 4 and the data acquisition and positioning system 5, and to move over the ground 6 allowing a continuous galvanic contact between the contact appendage 9 and the ground 6, while at the same time maintaining the electrical contact between the data acquisition and positioning system 5 and the reference electrode 2 by means of the first cable 8. To that end, the vehicle 3 can be implemented in different ways, for example, by means of a motor-driven electric vehicle, where it can be an autonomous vehicle or a remote controlled vehicle.

The vehicle may furthermore incorporate an adapter for coupling a watering hose, since the electric potential measurement system 1 may comprise a watering hose with a diffuser secured to the vehicle 3 for wetting the ground while the vehicle moves. Data acquisition is preferably accompanied by the wetting of the ground 6 on which the electric potential will be measured, such that a hose with a diffuser secured to the vehicle can gradually wet the ground 6 in front of the contact appendage 9 of the measurement electrode 4, such that the contact appendage 9 comes into contact with the already wet ground. Alternatively, it is possible to wet the ground 6 manually with a hose prior to data acquisition. If the conditions of electrical contact between the contact appendage 9 and the soil are good, there is no need to water the ground 6.

The electric potential measurement system 1 may include sensors for acquiring additional variables that complement the electric potential measurements so that they can be taken into account when analysing the electric potential data, such as, for example:

An infrared sensor placed in the vehicle 3, facing the ground, to continuously measure the temperature of the ground 6 over which the vehicle 3 passes, such that in addition to the electric potential datum, the temperature of the ground is obtained. This additional measurement can be used to confirm whether or not the temperature of the ground 6 has played a significant role during the survey (for example, if part of the surveyed ground 6 was in the shade and there is a difference of 5-10 degrees, it would be reflected in the electric potential measurements).

A combined temperature and ambient humidity sensor, which is part of the data acquisition and positioning system 5, and is used to record the temperature and humidity conditions of the survey.

Figure 2A:
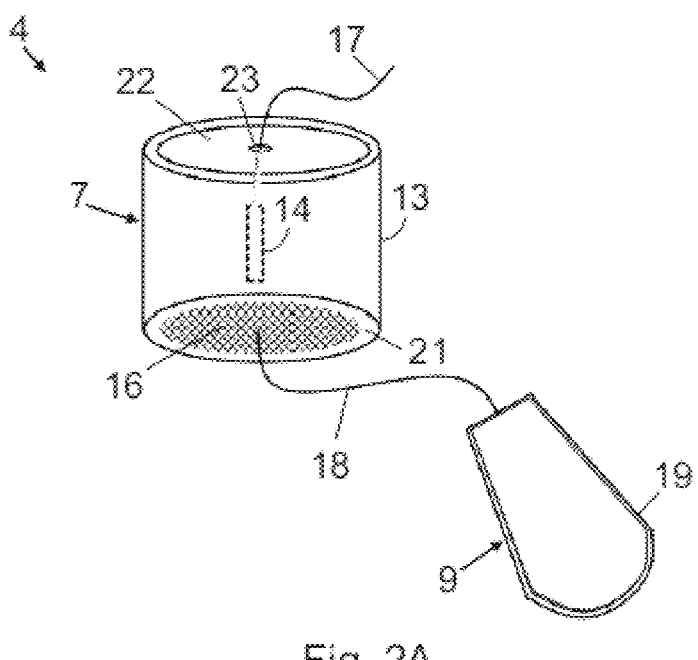
FIGS. 2A and 2B depict, according to one embodiment, the components of the measurement electrode of the electric potential measurement system.

FIG. 2A shows a measurement electrode 4 which is fixed to the vehicle 3, according to a possible embodiment. The measurement electrode 4 comprises a contact electrode 7 and a contact appendage 9.

Figure 2B:
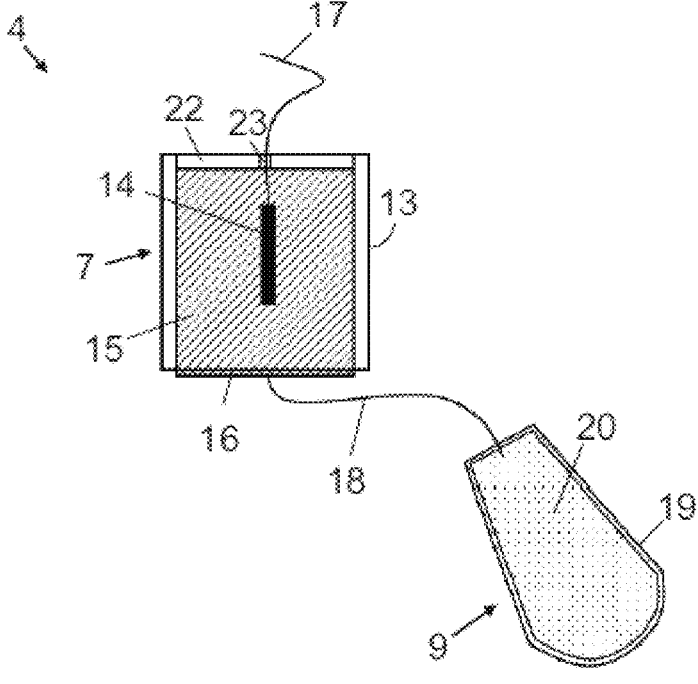

The contact electrode 7 is an electrode formed by a protective container 13 made of an electrically insulating material (preferably a plastic material, such as PVC) including therein a metal electrode 14 surrounded by a non-metal filler material (not shown in FIG. 2A), so that the metal electrode can remain in a relative chemical equilibrium therein. FIG. 2B shows the measurement electrode 4 of FIG. 2A, in which the contact electrode 7 and the contact appendage 9 are depicted with a longitudinal section to enable viewing the inside of the container 13, with the filler material 15 surrounding the metal electrode 14, and the filler material inside the contact appendage 9. The metal electrode 14 is in galvanic contact with the filler material 15.

The metal electrode 14 is an electrically conductive element, preferably made of stainless steel, although it can be manufactured from other metal materials such as copper, iron, steel, bronze, silver, titanium, gold, and/or graphite, among other materials. The metal electrode 14 is preferably completely surrounded by the filler material 15. Alternatively, the metal electrode 14 can be partially surrounded by the filler material 15. For example, the filler material can be contained in the container 13 until reaching a certain height of the metal electrode 14. The filler material 15 is a chemically stable non-metal material that does not react with the material of the metal electrode, and has an electrical conductivity less than the electrical conductivity of the metal electrode 14, preferably of several orders of magnitude lower, where it is a poor electrical conductor but without actually being an electrical insulator. For example, if the material of the metal electrode 14 is steel and the filler material 15 is a clay, the conductivity of steel is of the order of $10^6$ S/m and the conductivity of clay is of the order of $10^{-2}$ to 1 S/m, so the electrical conductivity of the filler material 15 is between 6 and 8 orders of magnitude lower. Other filler materials such as, for example, concrete, having a conductivity between $10^{-2}$ and $10^{-3}$ S/m, can be used, in which case the electrical conductivity of the filler material 15 could be between 8 and 9 orders of magnitude lower. The electrical conductivity of the filler material 15 is of at least 1 order of magnitude lower than the electrical conductivity of the metal electrode 14, and preferably between 6 and 14 orders of magnitude lower. The filler material 15 may have electrical properties equivalent to the electrical properties of sandy or clay soil or a combination of both, to the electrical properties of concrete, to the electrical properties of bentonite pellets, or to the electrical properties of wet bentonite powder, or it may be formed by one of these materials, among others.

The container 13 is preferably a cylindrical receptacle, although it may adopt another geometric shape. The embodiment of FIG. 2B shows the inner volume of the container 13 which is completely filled with the filler material 15, although it could also be partially filled. The container 13 is open on the base 21 thereof. The lower opening (i.e., the base 21 or lower face) of the container 13 is covered by a retaining mesh 16 which allows containing the metal electrode 14 immersed in the filler material 15 (e.g., wet bentonite periodically wet with water) inside the container 13. On the upper face, the container 13 has a cover 22 with an opening 23 to allow for the passage of a second electrically conductive cable 17 connected to the metal electrode 14, so that the inside of the container 13 does not lose any moisture and its temperature is maintained for as long as possible during the survey. A PVC or foam cover can be used, for example, in order to allow wetting same with water in the event that the filler material 15 on the inside (e.g., clay material) dries up or has not been used in a survey for a long time.

The retaining mesh 16 is made of a non-metal material which allows, on one hand, mechanically retaining the filler material 15 (and therefore, the metal electrode 14) inside the container 13 so that it does not fall out due to the effect of gravity, and at the same time allowing a non-metal electrical contact of the filler material 15 with the outside, that is, with whatever the retaining mesh 16 is in contact with outside the container. The retaining mesh is manufactured from a material that is not electrically insulating to allow a good non-metal electrical contact (in this case, with a third electrically conductive cable 18 connecting with the contact appendage 9). For example, the retaining mesh 16 can be a continuous layer of fabric (although it will have, by default, certain porosity, space between wires) allowing a certain degree of direct contact between the filler material 15 and the third conductive cable 18. The retaining mesh 16 can be manufactured from a different material, for example, a ceramic material.

The metal electrode 14 is spaced from the base of the container 13, i.e., it does not touch the base, such that it is floating inside the container, retained by the filler material 15. The contact electrode 7 rests on an electrically insulating support of the vehicle 3 and does not directly contact the soil. Galvanic contact with the ground 6 is carried out through the contact appendage 9.

The second electrically conductive cable 17 (made of a metal material, for example, copper) is in contact with the metal electrode 14 included inside the container. This second cable 17 carries the potential of the measurement electrode 4 to the data acquisition and positioning system 5. In particular, the first cable 8 can be connected to an input of an A/D converter of the data acquisition and positioning system 5 and the second cable 17 can be connected to the other input of said A/D converter to close the circuit and to enable measuring the electric potential difference at each point of the surface of the ground 6 surveyed by the contact appendage 9 with respect to the reference electrode 2.

The contact appendage 9 is made of a non-metal material and has a morphology suitable for being dragged along the soil and to maintain continuous galvanic contact with the soil while the vehicle 3 moves, thereby obtaining continuous measurements of the potential of the ground 6.

Figure 3:
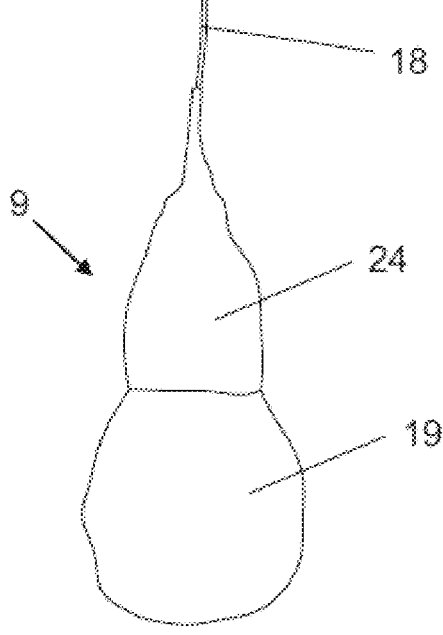
FIG. 3 shows a contact appendage for continuous measurement.

The contact appendage 9 is connected to the retaining mesh 16 by means of a third electrically conductive cable 18 (e.g., a metal cable made of copper or another material). In one embodiment, the contact appendage 9 is made up of a fabric covering 19 that is flexible (to enable the adaption thereof to the surface of the ground 6, since it is in charge of directly contacting the ground 6), has an antistatic behaviour (preferably not completely synthetic and contains cotton), and is filled with a textile material (fabric filler 20) formed by an absorbent fabric so that it can retain moisture, given that the contact appendage 9 must be able to stay wet. In this case, since it is not subject to friction, the fabric filler 20 does not have to be antistatic. FIG. 3 shows an example of a contact appendage 9 for continuous measurement. The upper part of the contact appendage 9, which does not contact the soil, presents a reinforcement 24 which can be made up of a plastic material (insulating band, etc.), to provide rigidity to the upper part of the covering 19 and furthermore to protect the connection of the third cable 18.

The function of the contact appendage 9 is to make uninterrupted contact with the ground 6 for continuously measuring the potential of the ground 6. The objective of the combination of the contact electrode 7 and the contact appendage 9, with their respective elements and interconnection through the third cable 18, is to cancel the polarisation effect in the contact between the ground 6 and the measurement electrode 4, so as to enable measuring the electric potential on any surface, avoiding the unwanted polarisation effect and with the signal that is as stable and as repeatable as possible. To manage polarisation, the element directly contacting the soil (contact appendage 9) must be a non-metal element. The contact surface of the contact appendage 9 with the ground 6, made at least partially of the flexible fabric covering 19, determines the resolution of the electric potential measurement, given that the obtained potential value corresponds approximately with the mean potential of the contact area of the measurement electrode 4 with the surface of the ground 6. The contact surface may vary based on the objective pursued; for example, the contact surface may have the size of a hair if a crack is to be located or a much larger size if an airport is surveyed to check for contamination in the soil.

However, the contact appendage 9 alone is not sufficient to obtain a good electric potential measurement of the ground 6. The signal coming only from the non-metal contact appendage 9 is unstable; however, when this signal is passed through the contact electrode 7, the signal stabilises. The present invention therefore proposes that the signal follows the following path:

Ground 6—contact appendage 9 (e.g., fabric).

Contact appendage 9—third electrically conductive cable 18 (e.g., copper).

Third cable 18—retaining mesh 16 (e.g., interface or layer of fabric). The third cable 18 directly contacts the retaining mesh 16. Advantageously, the use of the retaining mesh 16 allows maintaining contact without any relative movement over time. If the retaining mesh 16 were absent and the end of the third copper cable 18 were inserted into the filler material 15, said copper end could move inside the filler material 18 while measurements are being made, so the polarisation of the copper would change continuously and the measurements would not be precise.

Retaining mesh 16—filler material 15 (e.g., bentonite).

Filler material 15—metal electrode 14 (e.g., stainless steel).

Metal electrode 14—second electrically conductive cable 17 (e.g., copper).

Second cable 17—measurement equipment.

The electric current must necessarily move through all these components until reaching the measurement equipment of the data acquisition and positioning system 5 to thereby minimise the polarisation effect and furthermore obtain a stable signal.

Figure 4A:
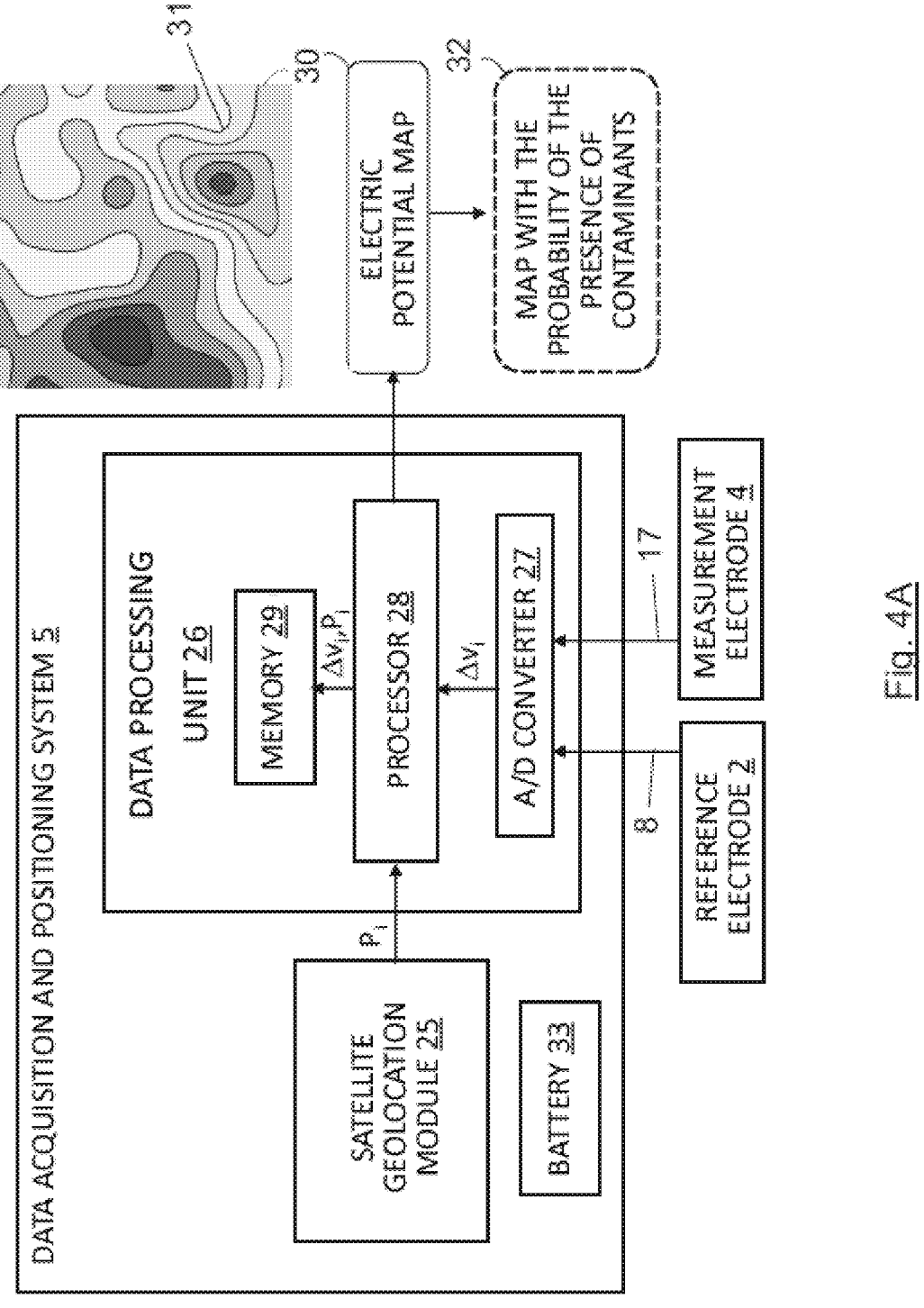
FIGS. 4A and 4B depict a diagram with the components of the data acquisition and positioning system, according to two possible embodiments.

FIG. 4A depicts the components of the data acquisition and positioning system 5 according to a possible embodiment. According to this embodiment, the data acquisition and positioning system 5 comprises a satellite geolocation module 25, configured for acquiring a plurality of position data $P_i$ of the vehicle 3 as it moves over the ground 6, and a data processing unit 26. These electronic components are powered by a battery 33 installed in the vehicle 3, which can be part of the data acquisition and positioning system 5 itself (as shown in the embodiment of FIG. 4A) or an external element (for example, the very battery of the vehicle 3 could be used if the vehicle has a battery).

The data processing unit 26 is configured for obtaining a plurality of electric potential difference measurements $\Delta v_i$ between the reference electrode 2 (the potential of which is measured through the first cable 8) and the measurement electrode 4 (the potential of which is measured through the second cable 17) as the vehicle 3 moves over the ground 6, according to a specific sampling frequency, for example.

The data acquisition and positioning system 5 is configured for storing in at least one memory the electric potential difference measurements $\Delta v_i$ and the position data $P_i$ of the vehicle 3 that are acquired. For example, as will be shown in the example of FIG. 5, the satellite geolocation module 25 can store in a memory the position data $P_i$ of the vehicle 3, and the data processing unit 26 can in turn store in another different memory the electric potential difference measurements $\Delta v_i$. In the embodiment shown in FIG. 4A, the data processing unit 26 stores both data ($\Delta v_i$, $P_i$) in a single memory 29. This data ($\Delta v_i$, $P_i$) which is stored in the memory can be used to obtain an electric potential map 30.

In this particular embodiment, the data processing unit 26 is additionally configured for obtaining an electric potential map 30 of the ground 6 by means of associating the electric potential difference measurements $\Delta v_i$ with the position data $P_i$ of the vehicle 3 that are acquired. In the electric potential map 30, the levels of the ground 6 having the same electric potential value are depicted by means of two-dimensional contour curves.

Optionally, the data processing unit 26 can additionally be configured for obtaining, from the electric potential map 30, a map 32 with the probability of the presence of contaminants (e.g., oils) in the subsoil of the surveyed ground 6, where said probability depends on the value of the electric potential measured at each surveyed point of the ground 6, besides other factors that may depend on the specific type of contaminant to be detected, surface effects associated with buried services (pipes, etc.), the geology of the ground, the depth of the water table, etc.

According to one embodiment, the data processing unit comprises an analog-to-digital converter 27, a processor 28, and a memory 29, where the analog-to-digital converter 27 can be part of the processor 28 itself or an independent unit, as shown in the example of FIG. 4A. The analog-to-digital converter 27 receives as inputs the analog potentials coming from the reference electrode 2 and the measurement electrode 4 (through the first cable 8 and second cable 17, respectively), and performs the conversion to a digital signal containing information about the electric potential difference $\Delta v_i$ between both electrodes (2, 4), which is representative of the electric potential value. The processor 28 receives the position data $P_i$ and stores it together with the electric potential difference measurements $\Delta v_i$ in the memory 29.

In one embodiment, the position data $P_i$ and the electric potential difference measurements $\Delta v_i$ are acquired in a synchronised manner, such that the processor 28 acquires them simultaneously in the same instant. For example, when the processor 28 receives a position datum $P_i$ coming from the satellite geolocation module 25, the processor 28 acquires in the same instant an electric potential difference measurement $\Delta v_i$ coming from the analog-to-digital converter 27. The position data $P_i$ and the electric potential difference data $\Delta v_i$ are thus directly associated and it is not necessary to perform any interpolation.

According to the embodiment shown in FIG. 4A, the processor 28 receives the position data $P_i$ of the vehicle 3 and the electric potential difference measurements $\Delta v_i$ for generating, by means of the association thereof, an electric potential map 30 of the ground 6, which two-dimensionally depicts the electric potential value, expressed in millivolts (mV), for example, for different positions of the surveyed ground 6. The contour curves (isolines 31) indicate the levels of equal electric potential value. Each isoline 31 has associated therewith a specific electric potential value, preferably expressed by means of colour variation, as depicted in the example of FIG. 4A.

When the system is applied to the detection of contaminants in the subsoil, for example of oils, a colour code can be used in the electric potential map 30 to represent the probability of the presence of oils, which is determined based on the value of the measured electric potential, thereby obtaining a map 32 with the probability of the presence of contaminants. For example, it can increase from blue to red as the probability of the presence of oils increases.

Figure 4B:
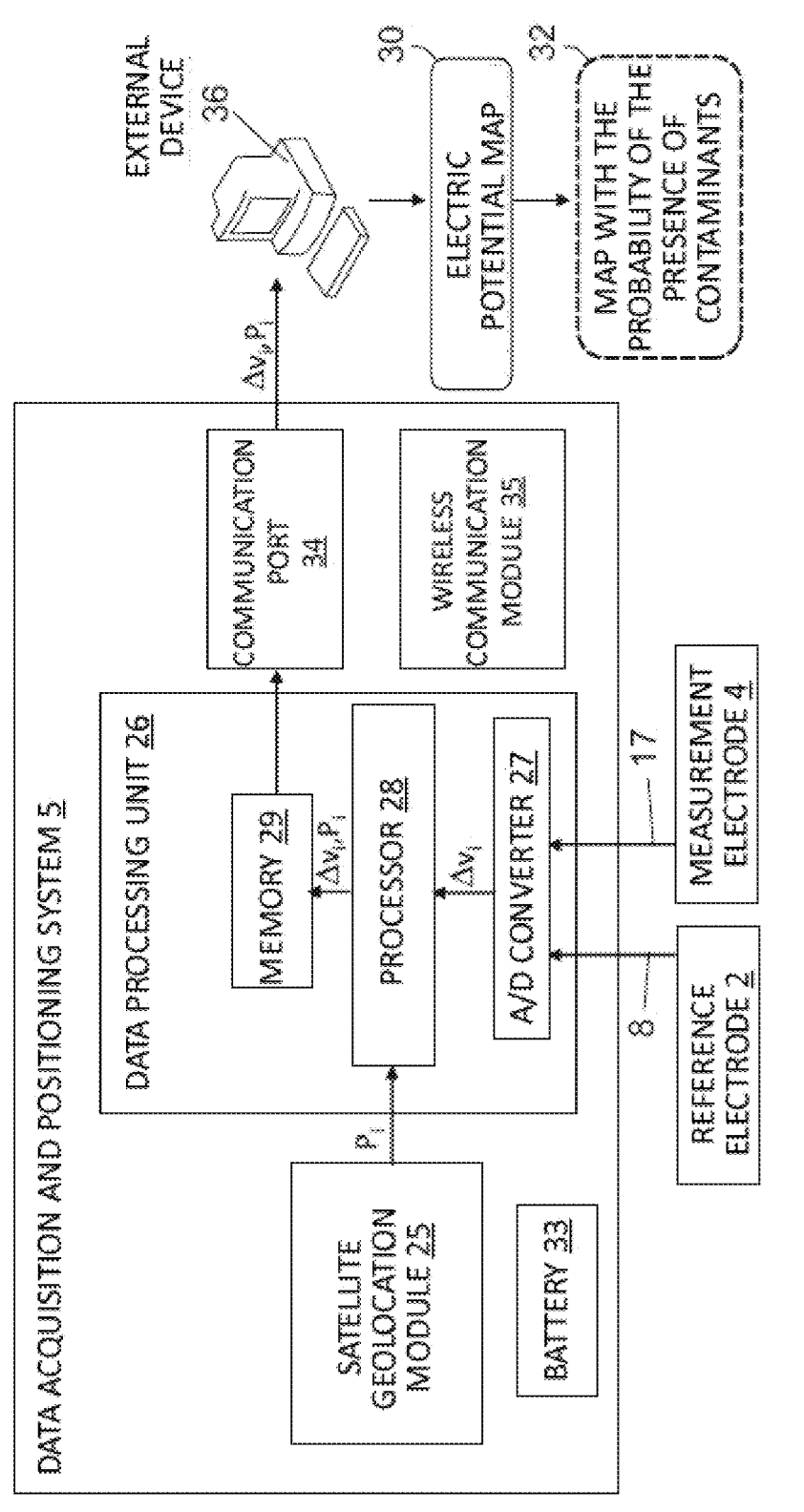

FIG. 4B depicts another embodiment in which the electric potential map 30 is not obtained by the data acquisition and positioning system 5, but rather by an external device 36, for example, a computer.

In this case, the data acquisition and positioning system 5 comprises at least one communication unit configured for transmitting the electric potential difference measurements $\Delta v_i$ and the position data $P_i$ of the vehicle 3 that are stored in the memory (for example, in memory 29 or in several memories) to the external device 36, which is in charge of processing the received data and obtaining, from said data, the electric potential map 30, and optionally a map 32 with the probability of the presence of contaminants in the subsoil of the surveyed ground 6. The at least one communication unit may comprise, among others, a cable communication port 34 (e.g., through a USB connector) and/or a wireless communication module 35 (e.g., by means of Bluetooth or Wi-Fi).

Figure 5:
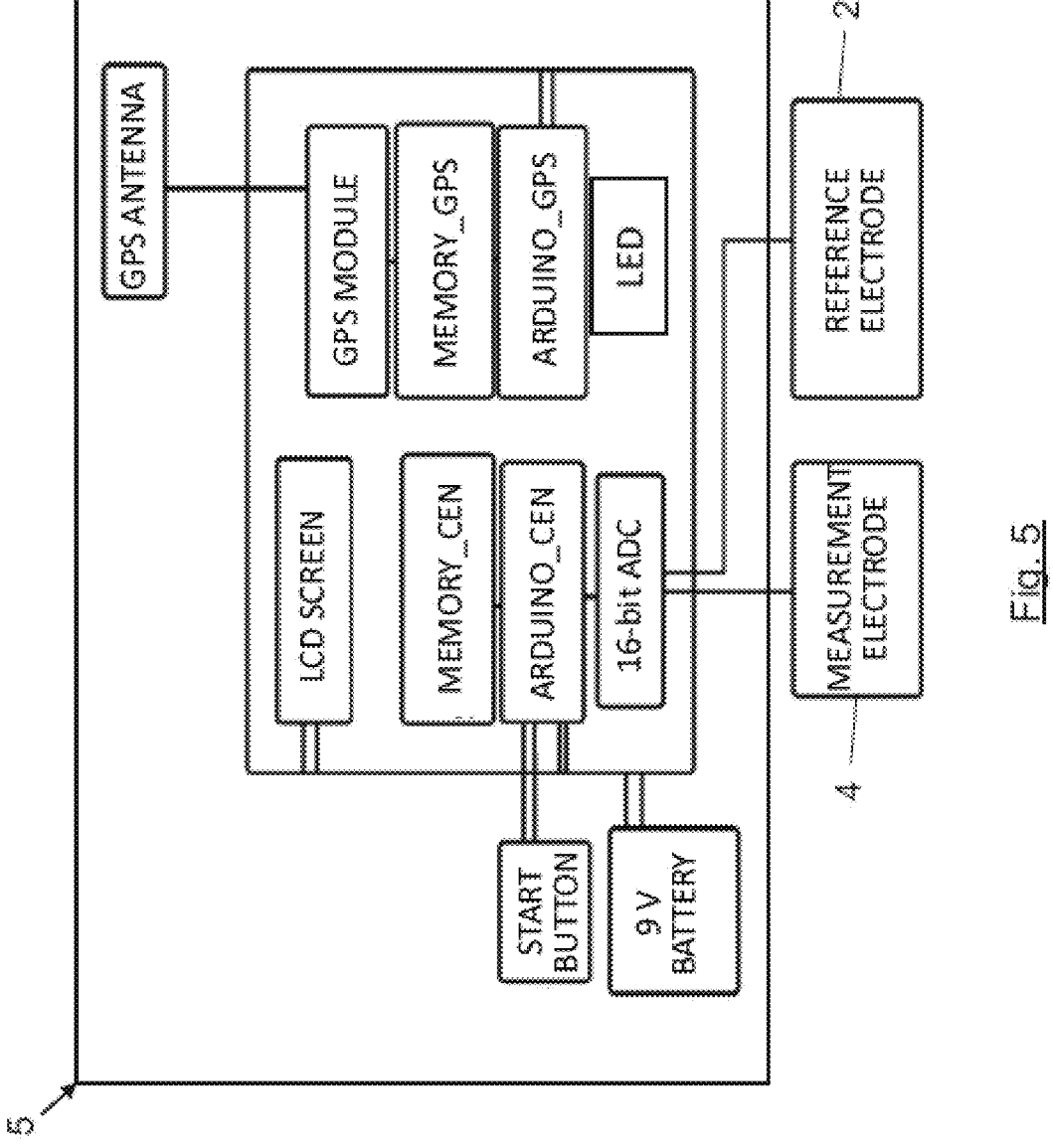
FIG. 5 illustrates a specific possible embodiment of the data acquisition and positioning system.

FIG. 5 shows a possible embodiment of the data acquisition and positioning system 5, the function of which is to acquire and record data relating to time, position, and potential difference in memory cards for the subsequent downloading and processing thereof.

The data acquisition and positioning system 5 is powered by a battery. To allow energy savings, the system can work in two working modes: recording mode, in which the system acquires and records data, and standby mode in which the system stays idle, without recording data and therefore with minimum energy consumption.

In this example, the data acquisition and positioning system 5 comprises the following elements:

A/D converter (16-bit ADC): This converter is initialised with a ⅔ gain (measurement range between +−6.144 V) and resolution of 0.1875 mV/bit. It is configured for measuring, at 250 samples/second, the potential differences of the measurement electrode 4 (located at the points where the electric potential is to be measured) with respect to the reference electrode 2 (point with respect to which the electric potential values are measured).

A first Arduino board (ARDUINO_CEN) with the following functions:

Reading the conversion results of the A/D converter without delay, digital filtering every 25 samples, and writing in a memory card (MEMORY_CEN). Data writing frequency observed: about 15 Hz.

Reading the state of the second Arduino board (ARDUINO_GPS).

Optionally, activating sound if there is RTK (Real Time Kinematic) precision in the position measurement while being in the recording mode at the same time.

MEMORY_CEN: SD card in which ARDUINO_CEN writes electric potential data.

Start button: a button, switch, or pushbutton which allows alternating between the recording mode and the standby mode.

A second Arduino board (ARDUINO_GPS) with the following functions:

Reading the data of the GPS module. Writing in a memory card (MEMORY_GPS).

Writing the state in LED pins and in ARDUINO_CEN.

MEMORY_GPS: SD card in which ARDUINO_GPS writes data relating to time and position.

GPS module: expansion boards with GPS functionality adapted for Arduino.

GPS antenna: antenna of the GPS module (e.g., multiband GNSS u-blox antenna, ANN-MB-00).

LCD screen: Showing data on the screen (time, number of measurement, electric potential data).

Battery: Powering the electronic components of the system. It is initialised at 9 V to ensure that all the components have enough energy.

LED: LED indicator of GPS precision quality (e.g., red=insufficient; yellow=FLOAT; blue=RTK).

The electronic circuit of FIG. 5 has the following functionalities:

Powering the system: once the battery is connected, connectivity check for the memory cards is performed and satellite search by the GPS is started.

Data recording start/stop button: recording mode or standby mode.

ARDUINO_CEN (recording mode): measuring and saving in an SD card the potential difference between two connections (electrodes) at a sampling frequency of about 15 Hz. Saving the internal time of the microprocessor for subsequent data cross-check.

ARDUINO_GPS (recording mode): measuring and saving in an SD card the GPS position at a sampling frequency of 1 Hz. Saving the internal time of the microprocessor for subsequent data cross-check.

Ring sound when the equipment is saving data and has RTK precision.

Displaying characters with relevant information on a 4×20 LCD screen. Recording mode: time, actual number of measurement, electric potential values. Standby mode: time, preceding number of measurement.

FIG. 5 is a merely illustrative embodiment of the data acquisition and positioning system 5 depicted in the overall diagram of FIGS. 4A and 4B. However, other multiple embodiments and implementations of the diagram of FIGS. 4A and 4B are possible, using different electronic components. For example, instead of a GPS-based absolute positioning system, a relative positioning system, independent of GPS coverage, based on inertial positioning (e.g., gyroscope and compass) and an odometry system can be used in one or more wheels of the vehicle 3 to know how far the body has moved, the direction in which it has moved, and the speed and acceleration at which it has moved.

The use of the electric potential measurement system 1, from on-site data acquisition to the representation of the electric potential map 30, is described below.

With respect to data acquisition, the installation of the reference electrode 2 is first carried out. The first step consists of localising a region inside or outside the survey area not having any buried service or installation nearby (water, electricity, pipes, etc.). Then, a borehole of about 50-100 cm in depth and diameter is made according to the morphology of the reference electrode 2 to be buried, which can be either a metal cylinder or a non-polarisable electrode.

The reference electrode 2 connected to a first cable 8 that reaches the surface is placed at the bottom of the borehole. This first cable 8 is then connected to the input of the A/D converter 27 of the data acquisition and positioning system 5, allowing the buried electrode to act as reference electrode for measuring the electric potential.

In anticipation of regions of the survey area that do not have GPS coverage (such as under the shelter of a service station, for example), a regular mesh can be plotted in said regions, marking the points of the mesh on the soil with spray. It relates to a relative positioning with respect to a point or a line, for example, a wall of a building, where the rows of regular mesh can be parallel to said wall, and the columns, perpendicular thereto. The wall of the building is usually geopositioned in the planes of installations. Alternatively, the relative position with respect to an object or shape located in a region with GPS coverage can also be referenced, such that relative coordinates can be transformed into UTM coordinates.

The next step is to cover the surface of the ground 6 to be surveyed with the passes of the vehicle 3. Data is acquired in generally parallel passes, whether in the form of rows or columns. Passes through regions having GPS coverage are usually oriented according to the plotting mesh of the preceding step (if some regions of the ground 6 do not have GPS coverage).

Figure 6:
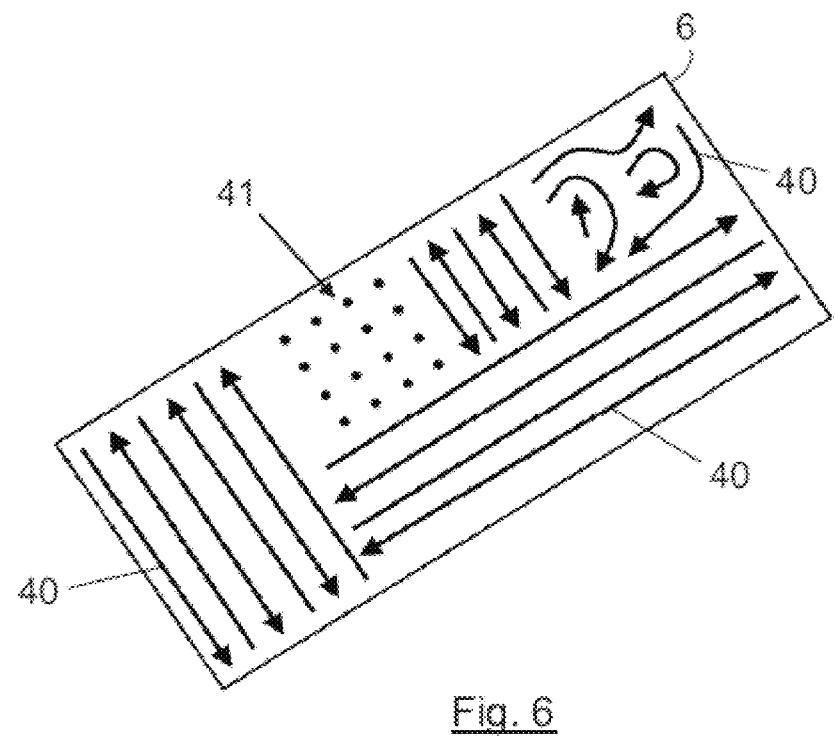
FIG. 6 shows an example of the geometry of the passes of the vehicle for acquiring data in a survey area.

FIG. 6 shows an example of the acquisition geometry, in which the survey area (ground 6 the electric potential of which will be measured) is depicted by a rectangle. Each pass 40 or movement of the vehicle 3 over the ground 6 is depicted by a solid line. In general, the passes 40 are parallel to the mesh made up of points corresponding to a region without GPS coverage (plotting mesh 40, in the top centre part of the survey area), but there may be passes 40 that do not follow the same pattern such as, for example those shown in the top right corner of the survey area.

Data acquisition is generally accompanied by the wetting of the ground 6 on which measurement will be made. A hose with a diffuser secured to the vehicle gradually wets the ground in front of the electrode, such that it comes into contact with the already wet ground. If the conditions of electrical contact between the electrode and the soil are good, watering is not required.

The first data pass, and alternately about every two passes, is what is known as the "control pass". It consists of repeatedly measuring the electric potential in a segment (of several meters) with the system installed in the vehicle, such that the relative evolution of the values of said segment (called "drift") can be used to correct the data over time.

Figure 7A:
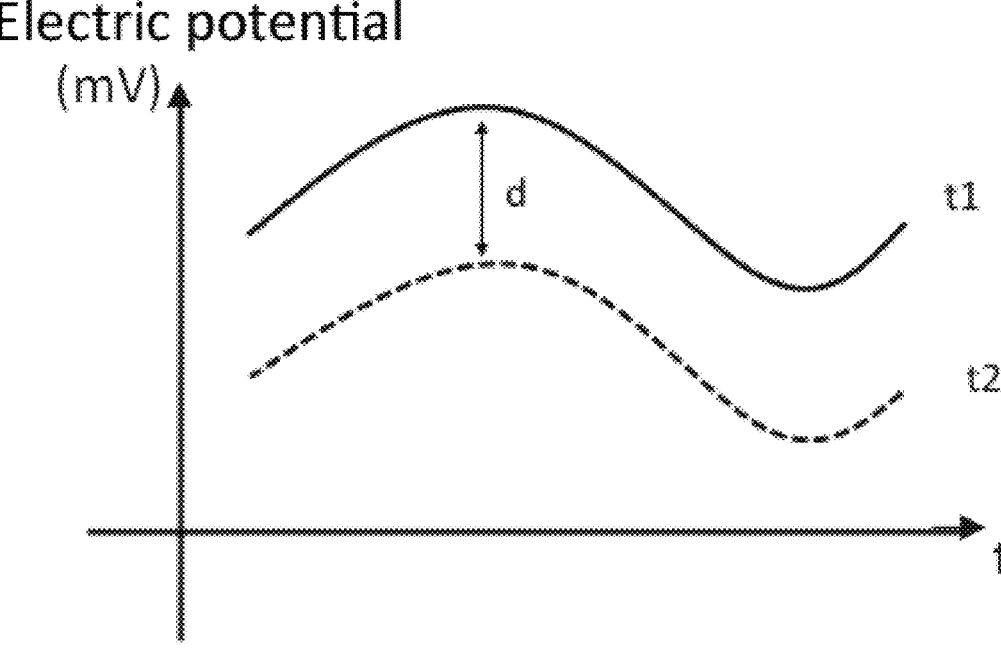
FIGS. 7A, 7B, and 7C show the acquisition of the electric potential in two control passes (FIG. 7A), the calculation of the drift as a function of time (FIG. 7B), and the application of the calculated drift in the electric potential measurements (FIG. 7C).

FIG. 7A shows the acquisition of the electric potential in two control passes for one same segment of the ground, but acquired in two different time instants, t1 and t2 (where t1 and t2 can represent, for example, the time instants at which each pass starts or the time instants at which each pass ends). The difference between both is the drift (d).

By repeating measurements on one same segment in different but not too distant time instants, it can be assumed that the variation of the electric potential over time is linear between two consecutive control points. To prevent the need to perform extrapolation, control measurements can be made before, during, and at the end of the measurements, such that only interpolation is required. The higher the frequency at which the control passes are performed, the more correct is the assumption of linearity between two measurements. If there is no significant electromagnetic noise, it is highly reliable to use this method for correcting possible low-frequency time variations the electric potential experiences (variations of the potential of the reference electrode 2 or of the potential of the measurement electrode 4, or time variations of the potential of the ground 6.

Figure 7B:
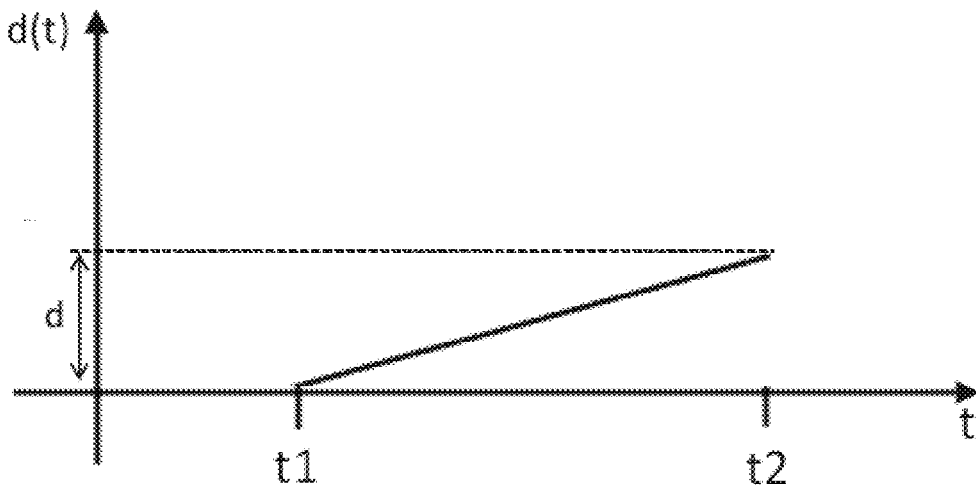

FIG. 7B shows the value of the drift d(t) calculated as a function of time, where it is assumed that the drift has evolved linearly between both time instants t1 and t2.

Figure 7C:
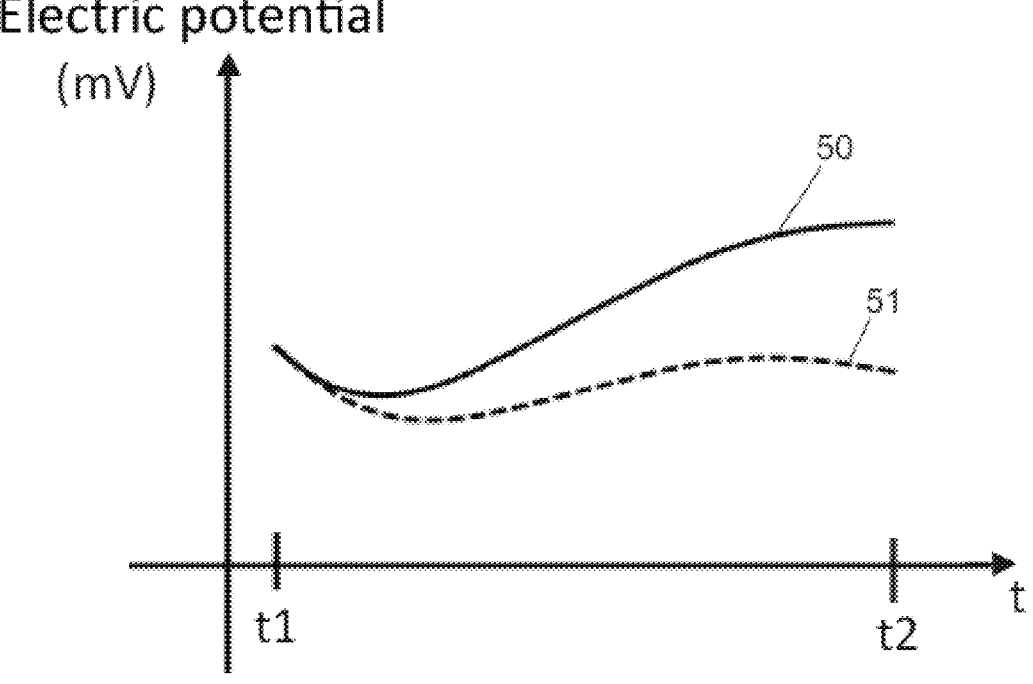

Therefore, and as depicted in FIG. 7C, once the drift (d) is calculated, the original electric potential signal 50 (solid line) measured, for example, in a pass 40, can be corrected by subtracting the drift (d) calculated as a function of time in FIG. 7B. The corrected electric potential signal 51 (dashed line) is the signal that would have been measured if there has been no evolution in the electric field between both time instants (t1 and t2).

FIGS. 8A and 8B show the examples of files for the data captured while surveying the ground 6 with the data acquisition and positioning system 5 of FIG. 5. The table of FIG. 8A illustrates an extract of the first three rows of a file of the ARDUINO_CEN of FIG. 5:

First column: pass number. A new datum (i.e., a new row, a new pass) is started every time when entering into the recording mode (by means of pressing the start button). While in the recording mode, the equipment continuously measures and writes the electric potential values and internal time in the row corresponding to the current datum number.

Second column: ARDUINO_CEN internal time (in ms) from the first time the recording mode is started. Although entering into the standby mode, the internal time is still being measured.

Remaining columns: electric potential data (each value is the rounded-up average of 25 data).

The table of FIG. 8B illustrates an extract of the first three rows of a file of the ARDUINO_GPS of FIG. 5:

First column: ARDUINO_GPS internal time (in ms) from the first time the recording mode is started. Although entering into the standby mode, the internal time is still being measured.

Second column: datum number. A new datum is written for every second that passes.

Third column: GPC "NMEA GNRMC" messages with information about the position of the vehicle.

In one embodiment, the position and electric potential data stored in one or more memories of the data acquisition and positioning system 5 are extracted by means of a cable through a communication port and/or by means of wireless communication (e.g., Bluetooth), to be processed by an external data processing unit (external device 36 of FIG. 4B) such as, for example, a computer.

Lastly, the electric potential map 30 is obtained and represented and this can be performed by the data acquisition and positioning system 5 itself or by an external data processing unit. To that end, the first step is (in the example of FIGS. 8A and 8B) comparing both (electric potential and position) data files to associate a position with each electric potential datum. To that end, the position data (X_UTM, Y_UTM) is interpolated at the same time as the electric potential data. The next step consists of presenting the electric potential data in space, preferably in a filled contour plot, although any other type is also possible.

The invention claimed is:

1. An electric potential measurement system for continuously measuring the electric potential of the ground, comprising:
    a reference electrode (2) buried in the ground (6) to be surveyed;
    a first electrically conductive cable (8) electrically connecting the reference electrode (2) with a data acquisition and positioning system (5);
    a vehicle (3);
    a measurement device (4) fixed to the vehicle (3) and comprising:
        a container (13) made of an electrically insulating material and having an opening at the base (21) of the container (13);
        a non-metal filler material (15) contained in the container (13);
        a non-metal retaining mesh (16) covering the base (21) of the container (13) and configured to retain the filler material (15) and allow a non-metal electrical contact between the filler material (15) and a third electrically conductive cable (18);
        a metal electrode (14) surrounded by and in galvanic contact with the filler material (15), the metal electrode (14) having an electrical conductivity greater than the electrical conductivity of the filler material (15);
        a second electrically conductive cable (17) electrically connecting the metal electrode (14) with the data acquisition and positioning system (5);
        a contact appendage (9) made of a non-metal material suitable for establishing a continuous galvanic contact with the ground (6) as the vehicle (3) moves over the ground (6) to be surveyed; and
        the third electrically conductive cable (18) electrically connecting the retaining mesh (16) with the contact appendage (9); and
    the data acquisition and positioning system (5), fixed to the vehicle (3) and comprising:
        a satellite geolocation module (25) configured for acquiring a plurality of position data (P$_i$) of the vehicle (3) as it moves over the ground (6); and a data processing unit (26) configured for obtaining a plurality of electric potential difference measurements (Δv$_i$), representative of the electric potential of the ground, between the first electrically conductive cable (8) of the reference electrode (2) and the second electrically conductive cable (17) of the measurement device (4) as the vehicle (3) moves over the ground (6);
wherein the data acquisition and positioning system (5) is configured for storing in at least one memory (29) the electric potential difference measurements (Δv$_i$) and the position data (P$_i$) of the vehicle (3) that are acquired.

2. The system according to claim 1, wherein the data processing unit (26) is additionally configured for obtaining an electric potential map (30) of the ground (6) by means of associating the electric potential difference measurements (Δv$_i$) with the position data (P$_i$) of the vehicle (3) that are acquired.

3. The system according to claim 1, wherein the data acquisition and positioning system (5) comprises at least one communication unit (34, 35) configured for transmitting the electric potential difference measurements (Δv$_i$) and the position data (P$_i$) of the vehicle (3) that are stored in the memory (29) to an external device (36).

4. The system according to claim 1, wherein the appendage comprises a fabric covering (19) with a filler (20) of textile material.

5. The system according to claim 1, wherein the filler material (15) includes at least one material selected from a sand or clay material, concrete, bentonite pellets, or wet bentonite powder.

6. The system according to claim 1, wherein the electrically insulating material of the container (13) is a plastic material.

7. The system according to claim 1, wherein the retaining mesh (16) is a layer of fabric.

8. The system according to claim 1, wherein the retaining mesh (16) is a layer of ceramic material.

9. The system according to claim 1, wherein the reference electrode (2) is a metal cylinder.

10. The system according to claim 1, wherein the reference electrode (2) is a non-polarisable electrode.

11. The system according to claim 1, comprising a watering hose with a diffuser secured to the vehicle (3) for wetting the ground (6) while the vehicle (3) moves.

12. The system according to claim 1, wherein the data processing unit (26) comprises an analog-to-digital converter (27), a processor (28), and a memory (29).

13. The system according to claim 1, wherein the position data (P$_i$) of the vehicle (3) and the electric potential difference measurements (Δv$_i$) are captured in a synchronised manner.

14. The system according to claim 1, wherein the data acquisition and positioning system (5) further comprises a relative positioning system based on an inertial positioning system and an odometry system in at least one wheel of the vehicle (3), wherein the relative positioning system is configured for acquiring the position data (P$_i$) of the vehicle (3) as it moves over the ground (6) when the satellite geolocation module (25) does not have satellite coverage.

\* \* \* \* \*